(12) United States Patent
Veasey et al.

(10) Patent No.: US 8,911,402 B2
(45) Date of Patent: Dec. 16, 2014

(54) DRUG DELIVERY DEVICE

(75) Inventors: Robert Veasey, Leamington Spa (GB); Garen Kouyoumjian, Leamington Spa (GB); Christopher Jones, Tewkesbury (GB); Catherine Anne Macdonald, Ashby-de-la-Zouch (GB); Marcus James Blachford, Leamington Spa (GB); James Andrew Holt, Leamington Spa (GB)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 273 days.

(21) Appl. No.: 13/498,905

(22) PCT Filed: Sep. 29, 2010

(86) PCT No.: PCT/EP2010/064424
§ 371 (c)(1), (2), (4) Date: Jul. 24, 2012

(87) PCT Pub. No.: WO2011/039231
PCT Pub. Date: Apr. 7, 2011

(65) Prior Publication Data
US 2012/0283645 A1    Nov. 8, 2012

(30) Foreign Application Priority Data

Sep. 30, 2009 (EP) .................................... 09171764

(51) Int. Cl.
*A61M 1/00* (2006.01)
*A61M 5/20* (2006.01)
*A61M 5/31* (2006.01)

(52) U.S. Cl.
CPC ............... *A61M 5/20* (2013.01); *A61M 5/3129* (2013.01); *A61M 5/3146* (2013.01); *A61M 2005/2073* (2013.01); *A61M 2205/6063* (2013.01)
USPC ............................ 604/122; 604/207; 604/189

(58) Field of Classification Search
USPC .......... 604/122, 124, 125, 207–211, 246, 404
See application file for complete search history.

(56) References Cited

U.S. PATENT DOCUMENTS 4,553,962 A * 11/1985 Brunet .......................... 604/198
8,075,515 B2 * 12/2011 Matusch ......................... 604/68
2009/0275916 A1   11/2009 Harms et al.

FOREIGN PATENT DOCUMENTS

DE    102005018305    12/2005
DE    102007031714     1/2009
(Continued)

OTHER PUBLICATIONS

European Search Report for European App. No. 09171764, completed Mar. 2, 2010.
International Search Report for International App. No. PCT/EP2010/064424, completed Mar. 11, 2011.
(Continued)

*Primary Examiner* — Kevin C Sirmons
*Assistant Examiner* — Deanna K Hall
(74) *Attorney, Agent, or Firm* — McDonnell Boehnen Hulbert & Berghoff LLP

(57) ABSTRACT

A drug delivery device comprising: a device body, an operating member which is configured to be movable relative to the device body for operating the drug delivery device, a preventing member which prevents movement of the operating member relative to the device body for operating the drug delivery device, wherein the preventing member is removable to allow movement of the operating member relative to the device body for operating the drug delivery device.

15 Claims, 4 Drawing Sheets

(56) References Cited

FOREIGN PATENT DOCUMENTS

| WO | 2004/028598 | 4/2004 |
| WO | 2007/050281 | 5/2007 |
| WO | 2007/066152 | 6/2007 |

OTHER PUBLICATIONS

International Preliminary Report on Patentability for International App. No. PCT/EP2010/064424, completed Dec. 13, 2011.

* cited by examiner

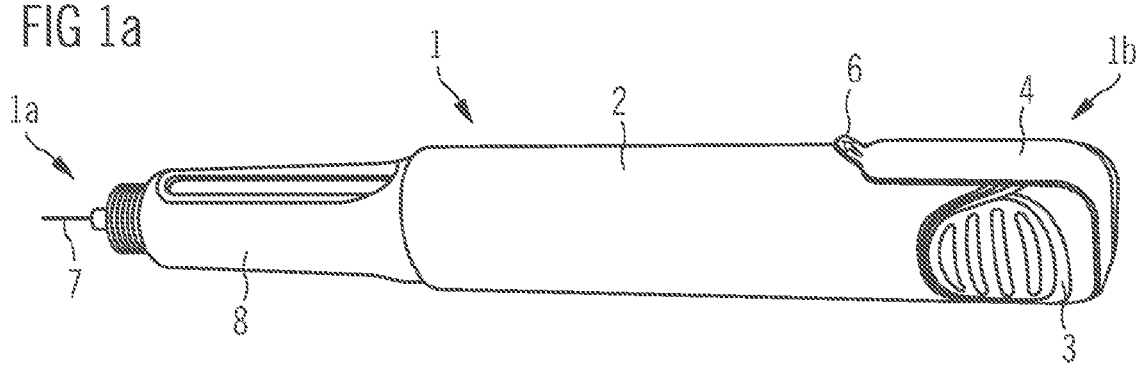
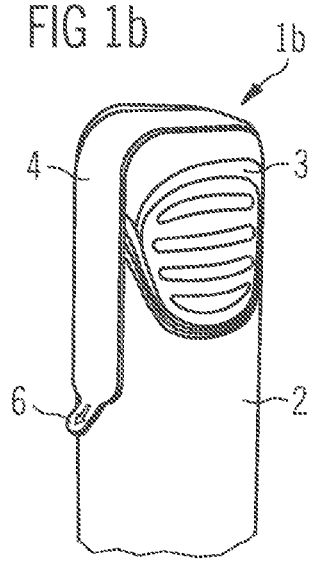
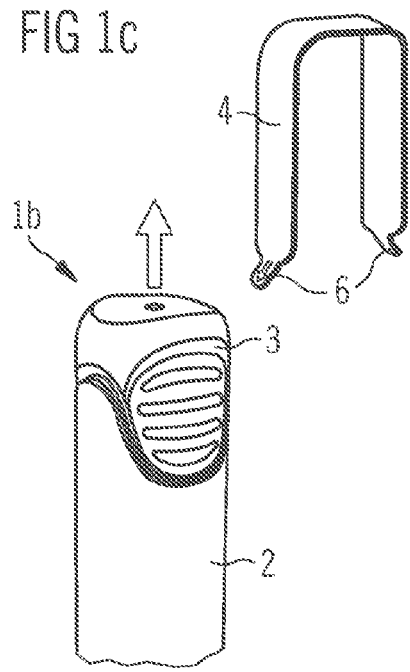

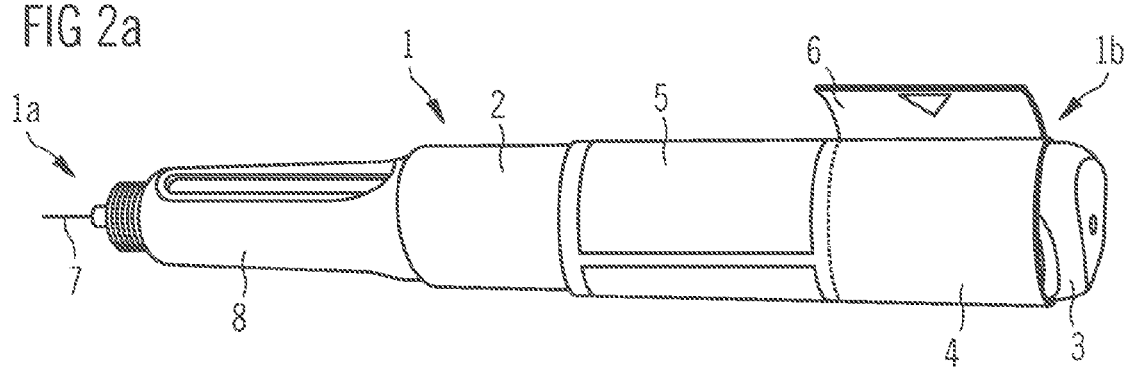
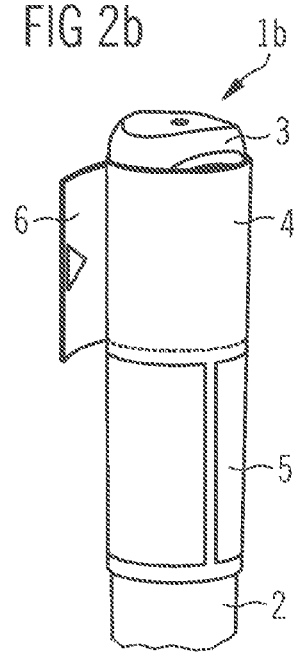
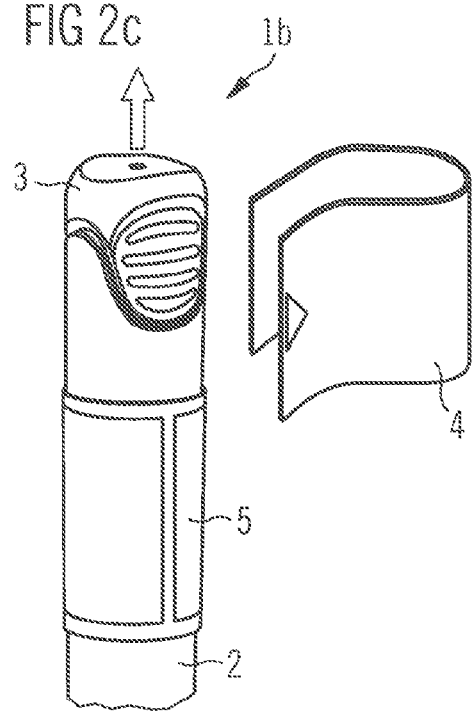

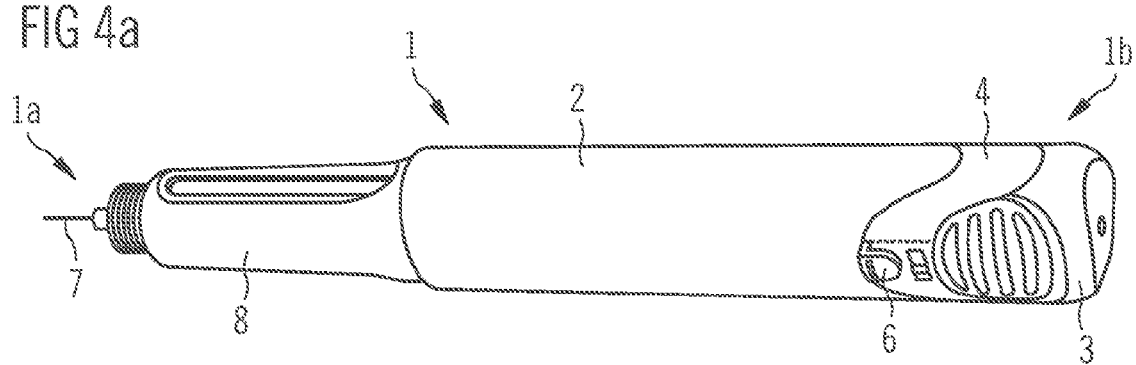
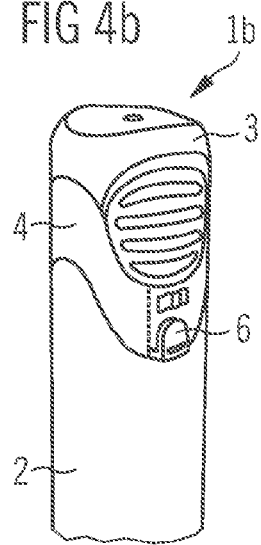
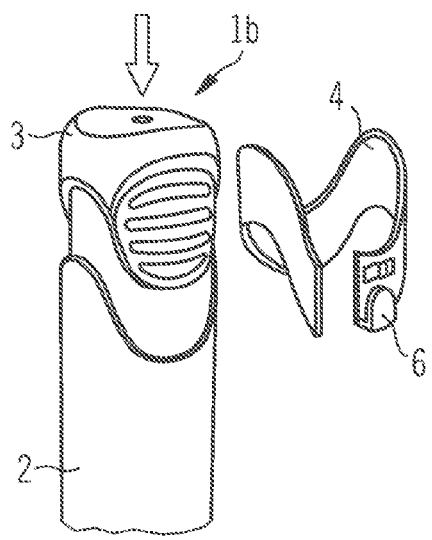

DRUG DELIVERY DEVICE

CROSS REFERENCE TO RELATED APPLICATIONS

The present application is a U.S. National Phase Application pursuant to 35 U.S.C. §371 of International Application No. PCT/EP2010/064424 filed Sep. 29, 2010, which claims priority to European Patent Application No. 09171764.5 filed on Sep. 30, 2009. The entire disclosure contents of these applications are herewith incorporated by reference into the present application.

FIELD OF INVENTION

The present disclosure relates to a drug delivery device which comprises a preventing member which prevents movement of an operating member relative to the device body.

BACKGROUND

U.S. Pat. No. 4,553,962 A discloses an automatic syringe comprising a C-shaped clip releasably fitted to a housing. DE 102007031714 A1 shows a single-use injector.

One problem of a drug delivery device is that the user cannot see if the device is in a primed or un-primed condition. That means that the user does not know if he has primed the device before or not. So the user cannot see if he has to perform a priming step before he can use the device in a correct way.

For example, users who are unfamiliar with the drug delivery device may forget to prime the device before dispensing the first dose. In case that the drug delivery device is, for example, an injector, and if the user does not prime the device before the first use, the user may inject an incorrect volume of drug during the first injection. This could happen because in an un-primed condition there may be gaps between the different parts of the device which are taken up when the device is operated for the first time to set or dispense the drug. These gaps may be a consequence of the manufacturing or assembling tolerances. These gaps may be considerable before the first operation but may be less considerable or not present at all afterwards.

Priming the device means that these gaps are reduced or removed by performing a priming step. After having performed the priming step, the device is in a primed condition so that the user can dispense the intended dose accurately.

SUMMARY

It is an object of the present disclosure to provide a drug delivery device which provides a user with information about whether a priming step was already performed or still has to be performed.

The drug delivery device may comprise a device body. The device body may be the base body of the device. In this device body, for example, an ampoule with a drug or the parts which are used for dispensing the drug, such as for example a piston rod may be arranged.

The drug delivery device may comprise an operating member. The operating member may be configured to be moveable relative to the device body. This operating member may be configured for operating the drug delivery device. Operating the device may mean that the dispensing of the drug may be initiated by, for example, moving the operating member relative to the device body, for example axially.

The drug delivery device may comprise a preventing member. This preventing member may prevent movement of the operating member relative to the device body. So, for example, the preventing member prevents the operation of the drug delivery device. For example the preventing member may prevent the movement of the operating member in a mechanical way. The movement of the operating member may be blocked by the preventing member.

In one embodiment of the drug delivery device the drug delivery device comprises a device body, an operating member which is configured to be moveable relative to the device body for operating the drug delivery device and a preventing member which prevents movement of the operating member relative to the device body for operating the drug delivery device, wherein the preventing member is removable to allow movement of the operating member relative to the device body for operating the drug delivery device.

The preventing member is removable from the drug delivery device. Removable means that the preventing member may be removed permanently from the device. After the preventing member has been removed, the operating member can be moved relative to the device body. Therefore, after the preventing member has been removed, the drug delivery device may be regularly operated for drug delivery, in particular with high dose accuracy. It is also possible, that only a part of the preventing member is removed, that part which prevents the operation of the device, and another part, which does not prevent the operation of the device, stays for example on or in the device.

The device is expediently in an un-primed condition when the preventing member is present.

Therefore, the user may be informed about the priming condition through the presence of the preventing member. Additionally, the user may be prevented from using the drug delivery device without removing the preventing member prior to using it. Therefore, if the user sees that the preventing member is still on the device, he knows that he has to prime the device after he has removed the preventing member from the device.

The priming of the device is expediently allowed only when the preventing member is removed.

Preferably, it is not possible for the user to prime the device without destroying the preventing member when the preventing member is not removed. Therefore, the user knows that the device is in an un-primed condition when the preventing member has not been removed or destroyed. Therefore the preventing member may have the function of a seal.

The term "drug", as used herein, preferably means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exedin-3 or exedin-4 or an analogue or derivative of exedin-3 or exedin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-Y-glutamyl)-des(B30) human insulin; B29-N-(N-litho-cholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:
H-(Lys)4-des Pro36, des Pro37 Exendin-4(1-39)-NH2,
H-(Lys)5-des Pro36, des Pro37 Exendin-4(1-39)-NH2,
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;
or an Exendin-4 derivative of the sequence
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2)25, Asp28] Exendin-4(1-39)-(Lys)6-NH2;
or a pharmaceutically acceptable salt or solvate of any one of the afore-mentioned Exedin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

In one embodiment, the device can be primed when the preventing member is removed by moving the operating member relative to the device body, in particular in an axial direction, which may be the proximal or the distal direction for example. Particularly, according to this embodiment, it may be possible to prime the device and to remove the preventing member simultaneously by moving the operating member.

The priming step may be performed, for example by pushing the operating member such that it moves in the distal direction relative to the device body, or for example by pulling the operating member such that it moves in a proximal direction relatively to the device body, or by pulling the operating member such that it moves in a distal direction relative to the device body and subsequently pushing the operating member such that it moves in a proximal direction relative to the device body. Alternatively the operating member may be pushed along one side of the device body relative to the device body to perform the priming step. There are also embodiments possible in which the operating member has to be turned around an axis to prime or pre-prime the device. A pre-priming step is a step which has to be performed before the priming step may be performed.

In one embodiment the operating member is positioned such that after removal of the preventing member, a priming step can be instantly performed.

Therefore, after having removed the preventing member the user can directly prime the device in one step. This step may, for example, be a movement, e.g. pushing or pulling, of the operating member, whereby the operating member may be moved relative to the device body. For example, for priming the operating member may be moved in a proximal direction relative to the device body.

In another embodiment the operating member is positioned such that after the preventing member is removed, a pre-priming step is necessary before the priming step can be performed.

This pre-priming step could be, for example, a pushing or pulling of the operating member. So, for example, the operating member may have to be pulled out of the device body in the distal direction in a pre-priming step before it can be pushed into the device body in the proximal direction during the priming step.

Or, for example, the operating member has to be rotated in the pre-priming step before it can be pushed or pulled in the priming step.

In one embodiment the preventing member is arranged partly on the operating member and partly on the device body.

In particular, the preventing member may secure the operating member relative to the device body in a way that it cannot be moved relative to the device body, without destroying the preventing member.

In one embodiment the priming step or the pre-priming step may be initiated by removing the preventing member. For example the operating member may move into the distal direction by pulling the preventing member out of the device.

The preventing member may be clipped or may be glued on the operating member and/or the device body. Through the mechanical connection of the operating member and the device body by the preventing member, these two parts are mechanically secured relative to each other.

In another embodiment the preventing member is arranged circumferentially with respect to the operating member.

The preventing member may encircle the operating member, for example in a way that the user cannot access the operating member without removing the preventing member before. But the preventing member could also be arranged in a way that it just secures the operating member relative to the device body. For example the preventing member may be arranged in the area in which the operating member enters the device body.

In another embodiment of the drug delivery device the preventing member is arranged partly inside the device and partly outside the device.

For example, the preventing member may penetrate the operating member; the operating member being prevented from movement relative to the device body. The preventing member may be removed by gripping the outer part of the preventing member and removing the preventing member by pulling the preventing member out of the device. Therefore the preventing member may have for example the function of a cotter pin in one embodiment, which mechanically prevents the operating member from movements relative to the device body. The preventing member may be totally removed during this removing step.

In another embodiment the removable preventing member is connected to a label.

This connection may be a permanent or a non-permanent connection. Accordingly, the label may be removed together with the preventing member when the preventing member is removed from the device, or the label may remain on the device when the preventing member is removed. The preventing member and the label may be non-permanently connected, e.g. via a perforation or tear strip.

In another embodiment information for using the device is provided on the label.

The information may comprise text and/or symbols. In case the label remains on the drug delivery device after removal of the preventing member the user can still get information about the correct use of the device from the information which is provided on the label. The label could be arranged, for example, on the device body. The label could be glued to the device, for example.

In another embodiment information about how to prime the device is provided on the preventing member.

The information comprises text and/or symbols, for example. The information may comprise information about performing the priming step or the pre-priming step, so the user can gather the information which may be necessary for priming directly from the preventing member. The user does not have to consult the instructions to get said necessary information. Therefore, the preventing member in combination with the information provided on the preventing member gives a high level of safety for the correct use of the device.

In another embodiment the task of the preventing member may primarily be warning the user rather than preventing actuation of the device by mechanical means. Warning the user may particularly involve information on the preventing member or on a label attached to the preventing member. According to this embodiment, the preventing member is particularly located on the operating member and/or the device body; usually no material connection between preventing member and operating member or device body, for example by an adhesive, is present; often, the preventing member is also not arranged on the operating member or device body in a form-fitting way. However, in a further embodiment the task of the preventing member may also be primarily preventing actuation of the device by mechanical means.

In another embodiment the preventing member comprises a grip-tab.

Grip-tabs could be arranged, for example, at one or more ends of the preventing member. The grip-tab may make it easier for the user to remove the preventing member from the device. The grip-tab may also provide information to the user on how to handle the preventing member in the removing step. The grip-tab may, for example, stick out from the device, and/or may comprise a texture on its surface for better handling.

The preventing member may comprise a material like a plastic, a thermosetting material or a thermoplastic for example.

In another embodiment the primed device is a fixed dose device.

This means that the device always dispenses a pre-defined, non-user-variable, e.g. constant or varying dose of drug after the drug delivery device has been primed in a correct way. Therefore, the drug delivery device may, for example, be used for drugs which should always be administrated by the user in the same dose. In such a case it is important that the first dose has exactly the same volume as the following doses. Therefore, it is preferable that the drug delivery device is primed correctly. Therefore, it is particularly advantageous that when the user operates a device for the first time it is possible to see whether the device has been primed or not.

In one embodiment the device is a pen-type injector.

The pen-type injector may be an injector for single-use or multiple-use. The pen-type injector may comprise an ampoule when it is given to the user or may not comprise an ampoule. In case that the injector does not comprise an ampoule or it is an injector which is made for multiple-use, the user has to load the injector himself In case of a multiple-use injector, the user has to carry out a reset-step before the second and all following uses. Especially in these cases when the user has to load the injector himself or when a reset-step has to be done, it is possible that not all parts of the drug delivery device are exactly aligned with respect to each other. Thus, it is expedient to prime the device before dispensing the first dose.

There are embodiments possible, which may be provided with a new preventing member after a reset-step or a new loading of the device with a new ampoule.

Further features, advantages and expediencies become apparent from the following description of the exemplary embodiments in conjunction with the accompanying drawings.

BRIEF DESCRIPTION OF THE FIGURES

FIGS. 1a to 1c show a schematic view of a first embodiment of the drug delivery device in three different illustrations.

FIGS. 2a to 2c show a schematic view of a second embodiment of the drug delivery device in three different illustrations.

FIGS. 4a to 4c show a schematic view of a fourth embodiment of the drug delivery device in three different illustrations.

DETAILED DESCRIPTION

Figure 3A:
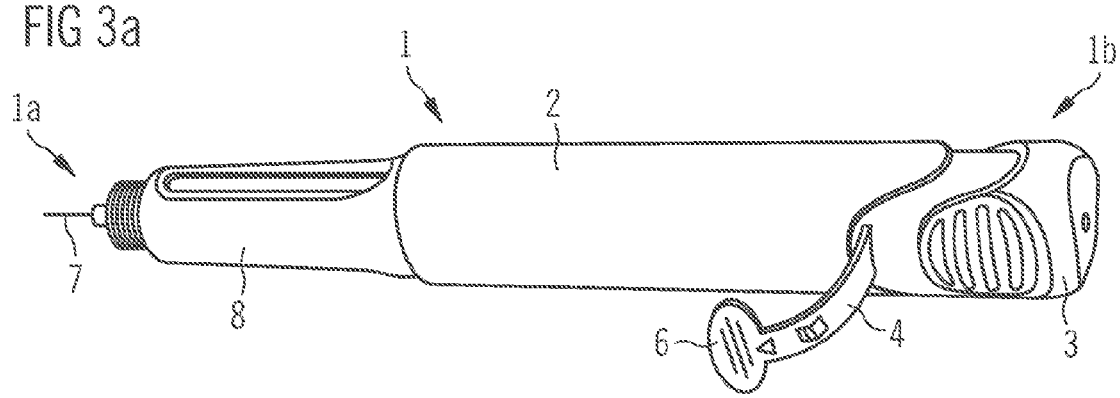
FIGS. 3a to 3c show a schematic view of a third embodiment of the drug delivery device in three different illustrations.

FIG. 1a shows a schematic view of the drug delivery device 1. The drug delivery device 1 comprises a device body 2 and a cartridge holder 8 located adjacent to the device body 2 in the distal direction. Furthermore, there is a needle 7 located at its distal end 1a and an operating member 3 at its proximal end 1b. In this embodiment the operating member 3 is a button. The drug delivery device 1 comprises a preventing member 4 in the form of a strip, having a first end on one side of the device body 2, extending around the operating member 3 at the proximal end 1b of the device and a second end on the other side of the device body 2.

FIG. 1b shows a more detailed view of the proximal section of the drug delivery device 1. The operating member 3 is secured in its position relative to the device body 2 by the preventing member 4, so that it cannot move relative to the device body 2, particularly in the proximal direction. The preventing member 4 comprises grip-tabs 6 at one or both ends that make it easier for the user to grip and to remove the preventing member 4. The preventing member 4 starts on one side of the device body 2, continues on one side of the operating member 3, surrounds the proximal end of the operating member 3, and continues and ends on the opposite side of the device body 2 from which it has started.

FIG. 1c shows the same view as FIG. 1b, however, now the preventing member 4 has been removed, for example by pulling at one of the grip-tabs 6. The preventing member 4 has a grip-tab 6 in this embodiment at both of its ends. The preventing member 4 is now totally removed from the drug delivery device 1 and no longer prevents the operating member 3 from being moved relative to the device body 2. The operating member is now movable, and can e.g. be pulled in the proximal direction relative to the device body 2. The pulling of the operating member 3 in the proximal direction may, for example, be a pre-priming step.

FIG. 2a shows a schematic view of a drug delivery device 1 having a different embodiment of the preventing member. The drug delivery device 1 comprises a needle 7 at its distal end 1a. It comprises a cartridge holder 8 which is arranged between the needle 7 and the device body 2. At the proximal end 1b the device comprises an operating member 3. The operating member 3 is a button in this embodiment. The middle part of the device body 2 is circumferentially surrounded by a label 5. The label 5 is connected at its proximal end, e.g. via perforation, to a preventing member 4 which circumferentially surrounds parts of the device body 2 and the operating member 3. The preventing member 4 comprises a grip-tab 6. By surrounding the operating member 3 and at the same time surrounding the proximal end of the device body 2, the preventing member 4 prevents the operating member 3 from being moved relative to the device body 2.

FIG. 2b shows a more detailed view of the proximal end of the device. The device body 2 is surrounded circumferentially by the label 5 which is connected at its proximal end to the preventing member 4. The preventing member 4 comprises a grip-tab 6. The operating member 3 which is circumferentially surrounded by the preventing member 4 is not able to move relative to the device body 2 in this condition, because it is secured e.g. by means of an adhesive by the proximal end of the preventing member 4.

FIG. 2c shows the same view as FIG. 2b, however, now the preventing member 4 has been permanently removed from the drug delivery device 1. The preventing member 4 has also been separated from the label 5 which still remains on the drug delivery device 1 and still surrounds the device body 2. Therefore, information for using the drug delivery device 1 or about the drug contained in the cartridge may be provided on the label. The operating member 3 is no longer fixed by the preventing member 4 and can now be, for example, pulled in the proximal direction. The pulling of the operating member 3 could, for example, be a pre- priming step. After the device has been primed it can be operated to set and deliver doses of drug by moving the operating member 3 relative to the device body 2.

FIG. 3a shows a schematic view of a third embodiment of the drug delivery device 1. The drug delivery device 1 comprises a needle 7 at its distal end 1a, a cartridge holder 8, a device body 2 and an operating member 3 at its proximal end 1b. The preventing member 4 is inserted into the drug delivery device 1. The preventing member 4 comprises a grip-tab 6 at its outer end.

Figure 3B:
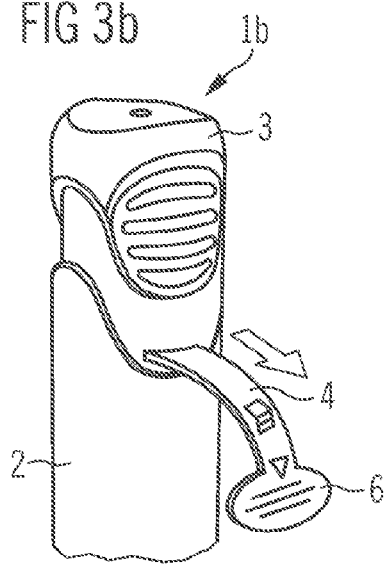

FIG. 3b shows a proximal section of the drug delivery device 1 which is shown in FIG. 3a. The preventing member 4 is inserted into the drug delivery device 1 in a location which prevents the operating member 3 from being moved in the distal direction relative to the device body 2. By taking the grip-tab 6 of the preventing member 4, the preventing member 4 can be pulled out of the drug delivery device 1 by the user.

Figure 3C:
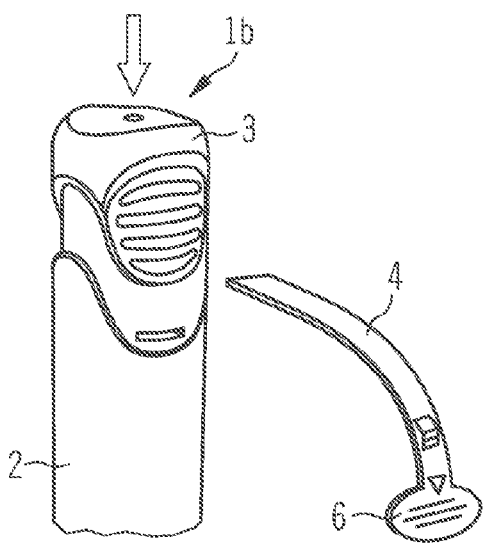

FIG. 3c shows the same section as shown in FIG. 3b, however, now, the preventing member 4 has been removed from the device and the operating member 3 is no longer prevented from being moved relative to the device body 2. The operating member 3 is in a "pre-primed position" in this embodiment. Thus, the operating member 3 can now be pushed directly in a distal direction relative to the device body 2. The pushing of the operating member 3 into the device body 2 may be the priming step.

FIG. 4a shows a schematic view of a fourth embodiment of the drug delivery device 1. The drug delivery device 1 comprises a needle 7 at its distal end 1a. It furthermore comprises a cartridge holder 8 and a device body 2. The operating member 3, which is a button in this embodiment, is located at the proximal end 1b. The preventing member 4 is arranged between the operating member 3 and the device body. The preventing member 4 comprises a grip-tab 6.

FIG. 4b shows a proximal section of the drug delivery device 1 which is shown in FIG. 4a. The preventing member 4 is located between the device body 2 and the operating member 3. The preventing member 4, which comprises a grip-tab 6, runs circumferentially around the drug delivery device 1 like a sleeve or a collar. The preventing member 4 has a perforated or thin region close to the grip-tap 6 arranged so that by pulling at the grip-tap 6 this region rips. Thereby, the preventing member 4 no longer forms a closed sleeve surrounding the device and may be removed easily by the user.

FIG. 4c shows the same section of the drug delivery device 1 which is shown in FIG. 4b. The preventing member 4 is now permanently removed from the drug delivery device, for example by pulling at the grip-tab 6. In this embodiment the operating member 3 is also in a "pre-primed position" relative to the device body 2. Therefore, the operating member 3 can now directly be pushed in the distal direction into the device body 2. By pushing the operating member 3 into the device body 2 the drug delivery device 1 may be primed.

The invention is not restricted to the exemplary embodiments by the description on the basis of said exemplary embodiments. Rather, the invention encompasses any new feature and also any combination of features, that in particular comprises any combination of features in the patent claims and any combination of features in the exemplary embodiments, even if this feature or this combination itself is not explicitly specified in the patent claims or exemplary embodiments.

The invention claimed is:

1. A drug delivery device that is configured to be primed in a priming step, wherein priming is a step carried out before injecting the first volume of a drug so that the user can dispense the intended dose accurately, the drug delivery device comprising:
   a device body,
   an operating member which is configured to be movable relative to the device body to perform two actions, a priming action and a dose delivery action, where the operating member is further configured such the priming action must occur before the dose delivery action,
   a preventing member which prevents movement of the operating member relative to the device body for operating the drug delivery device and which prevents the priming action,
   characterized in that the preventing member is removable from the drug delivery device to allow the movement of the operating member relative to the device body.

2. The device according to claim 1, wherein the device is in an un- primed condition when the preventing member is present.

3. The device according to claim 1, wherein priming the device is allowed only when the preventing member is removed.

4. The device according to claim 1, wherein the device can be primed when the preventing member is removed, by moving the operating member relative to the device body.

5. The device according to claim 1, wherein the operating member is positioned such that after the preventing member is removed, a priming step can directly be performed.

6. The device according to claim 1, wherein the operating member is positioned such that after the preventing member is removed, a pre-priming step is necessary before the priming step can be performed.

7. The device according to claim 1, wherein the preventing member is arranged partly on the operating member and partly on the device body.

8. The device according to claim 1, wherein the preventing member is arranged circumferentially with respect to the operating member.

9. The device according to claim 1, wherein the preventing member is arranged partly inside the device and partly outside the device.

10. The device according to claim 1, wherein the removable preventing member is connected to a label.

11. The device according to claim 10, wherein information for using the device is provided on the label.

12. The device according to claim 1, wherein information for priming the device is provided on the preventing member.

13. The device according to claim 1, wherein the preventing member comprises a grip-tab.

14. The device according to claim 1, wherein the primed device is a fixed dose device.

15. The device according to claim 1, wherein the device is a pen-type injector.

* * * * *